(12) United States Patent
Holmes et al.

(10) Patent No.: US 11,815,463 B1
(45) Date of Patent: Nov. 14, 2023

(54) REAGENT SYNTHESIS AND TESTING ASSAYS TO DETECT AND QUANTIFY MANGANESE (II)

(71) Applicants: Anna Merritt Holmes, Madison, AL (US); Emanuel Austin Waddell, Madison, AL (US)

(72) Inventors: Anna Merritt Holmes, Madison, AL (US); Emanuel Austin Waddell, Madison, AL (US)

(73) Assignee: Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 169 days.

(21) Appl. No.: 16/915,467

(22) Filed: Jun. 29, 2020

Related U.S. Application Data

(60) Provisional application No. 62/868,519, filed on Jun. 28, 2019.

(51) Int. Cl.
  *G01N 21/78* (2006.01)
  *G01N 21/31* (2006.01)
  (Continued)

(52) U.S. Cl.
  CPC ............... *G01N 21/78* (2013.01); *C08K 5/29* (2013.01); *C08L 5/00* (2013.01); *G01N 21/31* (2013.01); *G01N 33/18* (2013.01)

(58) Field of Classification Search
  CPC ........ G01N 21/78; G01N 21/31; G01N 33/18; C08K 5/29; C08L 5/00
  See application file for complete search history.

(56) References Cited

U.S. PATENT DOCUMENTS

| | | | |
|---|---|---|---|
| 4,965,191 A | * 10/1990 | Warren, III | ......... G01N 33/537 |
| | | | 436/811 |
| 9,528,983 B2 | 12/2016 | Holmes | |
| | | (Continued) | |

OTHER PUBLICATIONS

Rapid and Selective Spectrophotometric Determination of Manganese in Steels and Alloys Using Resacetophenone Oxime C. Kesava Rao, O. Babaiah, V. Krishna Reddy, T. Sreenivasulu Reddy Talanta, vol. 39, No. 10 1383-1385, 1992 (Year: 1992).*
(Continued)

*Primary Examiner* — Brian R Gordon
*Assistant Examiner* — Dwan A Gerido
(74) *Attorney, Agent, or Firm* — Maynard Nexsen PC; Brian T. Sattizahn

(57) ABSTRACT

The present disclosure relates to methods of detecting manganese in a solution using resacetophenone oxime by spectrophotometric analysis wherein the resacetophenone oxime produces colorimetric responses to indicate the presence of manganese. The resacetophenone oxime is not only stable in solution, but it also may be inserted into a hydrocolloid gel to facilitate a "spot test" for the detection of manganese, resulting in a long shelf life. These manganese testing methods disclosed herein may be used at the pre-disinfection process at water treatment facilities. The disclosed methods of manganese testing may be combined with an ammoniacal buffer reagent that may be used by water processing facilities, prior to final disinfection, to augment existing manganese (II) efforts of removal. A secondary flocculation with this buffer will scavenge additional manganese (II), that can then be removed by sedimentation or filtration.

15 Claims, 3 Drawing Sheets

(51) Int. Cl.
*G01N 33/18* (2006.01)
*C08L 5/00* (2006.01)
*C08K 5/29* (2006.01)

(56) References Cited

U.S. PATENT DOCUMENTS

2014/0061449 A1* 3/2014 Tunheim ............... G01N 21/94 250/573
2018/0230033 A1* 8/2018 Cumbie ............... C02F 3/2866

OTHER PUBLICATIONS

Spot Test for Detection of Manganese S.G. Kadarmandalgi Journal of Chemical Education, vol. 41, No. 8, Aug. 1964 (Year: 1964).*
Bouchard, M. F. et al., Intellectual Impairment in School-Age Children Exposed to Manganese from Drinking Water. Environ. Health Perspect. 2011,119 (1), 138-143.
Crossgrove, J. et al., Manganese Toxicity upon Overexposure. NMR Biomed. 2004, 17 (8), 544-553.
Duffin, Paul A. The Effect of Phytate on Mineral Bioavailability and Heavy Metal Contaminants, University of Surrey, 1989.
Guidelines for Drinking-Water Quality, 2nd ed.; International Programme on Chemical Safety of the World Health Organization, Ed.; WHO Office of Publications: Geneva, 1996; vol. 2.
Guilarte, T. R. Manganese Neurotoxicity: New Perspectives from Behavioral, Neuroimaging, and Neuropathological Studies in Humans and Non-Human Primates. Frontiers in Aging Neuroscience. 2013.
International Organization for Standardization. Water quality-determination of manganese. Geneva, 1986 (ISO 6333:1986 (E).
Kwakye. G. F. et al., Manganese-Induced Parkinsonism and Parkinson's Disease: Shared and Distinguishable Features. Int. J. Environ. Res. Public Health 2015. 12 (7), 7519-7540.
Munoz-Rocha, T. V. et al., Prenatal Co-Exposure to Manganese and Depression and 24-Months Neurodevelopment. Neurotoxicology 2018, 64, 134-141.
Neal, A. P. et al., Mechanisms of Lead and Manganese Neurotoxicity. Toxicol. Res. (Comb). 2013.2 (2).
Park, R. M. Neurobehavioral Deficits and Parkinsonism in Occupations with Manganese Exposure: A Review of Methodological Issues in the Epidemiological Literature. Sal. Health Work 2013, 4 (3), 123-135.
Pfalzer, A. C.; et al., Relationships Between Essential Manganese Biology and Manganese Toxicity in Neurological Disease. Current environmental health reports. 2017.
S. R. Cooper. Organic Synthesis—Resacetophenone; 1941; vol. 21.
Woker, G. On The Theory of Fluorescense. Zeit. phys. Chem. 1897, 24, 497.

* cited by examiner

REAGENT SYNTHESIS AND TESTING ASSAYS TO DETECT AND QUANTIFY MANGANESE (II)

CROSS-REFERENCE TO RELATED APPLICATION

This application claims priority to U.S. Provisional Patent Application No. 62/868,519, entitled "Reagent Synthesis and Testing Assays to Detect and Quantify Manganese (II)" and filed on Jun. 28, 2019, which is incorporated herein by reference.

BACKGROUND OF THE INVENTION

Manganese (Mn) is the twelfth most abundant element in the Earth's crust and belongs to a class of microbiogenic elements known as metallomes, which have key catalytic roles in enzyme function. Catalysts are not exhausted in the reaction process, however, and therefore if manganese is introduced at levels higher than required by an organism, it will hyperaccumulate. Although it is an essential, required trace metal in organisms, it becomes toxic at levels higher than 0.000017% by total body mass of the organism, a percentage that deviates very little between all organisms. For an average adult human male (approximately 185 lbs.) and female (approximately 135 lbs.), this toxic level calculates to Total Body Concentrations (TBC) of 14 mg and 10 mg, respectively.

If an individual hyperaccumulates manganese, the manganese will accumulate in the basal ganglia of the brain, which causes neurotoxicity and other pathologies. Manganism, a disease caused by manganese toxicity so closely resembles those of Parkinson's Disease that in older patients, particularly those consuming large doses of manganese in their multivitamins, a misdiagnosis of Parkinson's Disease is the norm rather than the exception. In infants and young children, inappropriate amount of manganese is associated with neurological delay/deficiency, attention deficit hyperactivity disorders (ADHD) or autism spectrum disorders (ASD). This is particularly evident in formula-fed infants due to the mandatory inclusion of manganese in all baby formula. But in the healthy youth to middle-age populations, the body has the ability to eliminate 1.6-2.0 mg of manganese daily, which is usually sufficient to prevent hyperaccumulation.

Given the danger of hyperaccumulation of manganese, the various modes of introducing manganese into the body are of key interest to public health. Non-occupational sources of chronic exposure to manganese include water, food, over-the-counter (OTC) vitamins/supplements, and magnetic resonance imaging (MRI) contrast materials. MRI contrast materials are used only on individuals that medically have a need for that procedure and are not a widespread means of accumulating manganese by the general population. Vitamin supplementation is more widespread and should not include a combination of vitamins that exceed an individual's daily requirement while taking into consideration natural sources of manganese from food and water. Manganese ingestion from plant sources with the affiliated bulk fiber, however, is often reduced in uptake because metal ions in the presence of phytates (antioxidant compounds from whole grains, nuts, legumes and seeds) can impair absorption by binding to certain dietary minerals such as iron, zinc, calcium and manganese, thus passing through the body without being absorbed. Of the remaining sources, the most biologically-active source of manganese—manganese (II)—is found in the water supply and may readily hyperaccumulate in the body.

In view of the danger of hyperaccumulation of manganese to population, particularly as a result of ingestion from the water supply, methods of testing the water supply and other solutions for the presence of manganese is critical. The approved Environmental Protection Agency (EPA) testing methods for the detection of manganese in water (atomic absorption, acetylene flame, electrothermal and inductively coupled plasma and persulfate methods) are toxic and difficult to perform outside of advanced analytical laboratories. This requires water treatment facilities to outsource these costly, specialized tests. The persulfate method, which is the only approved colorimetric method, uses toxic and controlled reagents, which are hazardous to store and handle, including mercury sulfate, concentrated nitric and phosphoric acids, silver nitrate and ammonium persulfate. As described in the *Standard Methods For The Examination of Water and Wastewater* the persulfate method (Method: 3500-Mn B) for quantifying manganese concentration in water, has a "low detection limit" of 0.210 mg/L. This detection limit, however, is an entire order of magnitude above the "maximum allowable limit" set for water for pharmaceutical use (WPU) or bottled drinking water (0.01 mg/L and 0.05 mg/L, respectively) established as a World Health Organization (WHO) global standard. Therefore, it is critical that a method for detecting manganese be developed that is simpler, more user-friendly, and less toxic than the current methods of detection.

SUMMARY OF THE INVENTION

In some embodiments, the present disclosure relates to methods of testing sample solutions for the presence of manganese. In some embodiments, the method of testing for the presence of manganese in a sample solution comprises the steps of: preparing at least one positive control, wherein the positive control contains manganese; preparing a negative control containing no manganese; adding resacetophenone oxime to the at least one positive control, negative control and the sample solution; incubating the at least one positive control, negative control and the sample solution; and measuring the at least one positive control, negative control and the sample solution for a colorimetric reaction, wherein a colorimetric reaction indicates the presence of manganese. In some embodiments of the method, the step of measuring the at least one positive control, negative control and the sample solution for a colorimetric reaction is performed using spectrophotometry.

In some embodiments, the step of preparing at least one positive control comprises preparing a series of two or more positive controls, ranging in manganese concentration from about 10 to 500 micrograms. In some embodiments, the positive controls comprise manganese concentrations of about 10, 50, 100, 250 and 500 micrograms. In some embodiments of the method, the resacetophenone oxime added to the at least one positive control, negative control and the sample solution is at a concentration of about 1 g/L.

In some embodiments of the method, the resacetophenone oxime is at a concentration of 0.2% w/v in 10% v/v ethanol water containing an ammoniacal buffer. In some embodiments of the method, the ammoniacal buffer is at a pH between about 8.24 and 10.0. In some embodiments of the method, the method is performed at room temperature. In some embodiments of the method, the incubation step is performed above room temperature.

In some embodiments of the method, the resacetophenone oxime is contained within a hydrocolloid gel, wherein the hydrocolloid gel is configured to at least partially dissolve upon adding the resacetophenone oxime to the at least one positive control, negative control and the sample solution. In some embodiments, the hydrocolloid gel comprises gellan gum.

In some embodiments of the method, the sample solution is obtained from a water supply. In some embodiments of the method, if a colorimetric reaction is observed in the sample solution, performing the additional steps of adding ammoniacal buffer to the water supply, wherein the ammoniacal buffer is at a pH of at least 9.25, to sediment manganese and filtering the sedimented manganese from the water supply.

In some embodiments, the present disclosure relates to kits for testing for the presence of manganese in a solution. In some embodiments, the kit comprises: a manganese positive control; a negative control containing no manganese; and resacetophenone oxime. In some embodiments, the kit further comprises a multi-well plate. In some embodiments of the kit, the resacetophenone oxime is contained within a hydrocolloid gel. In some embodiments of the kit, the hydrocolloid gel comprises gellan gum.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure relates to methods of detecting manganese in a solution using resacetophenone oxime by spectrophotometric analysis wherein the resacetophenone oxime produces colorimetric responses to indicate the presence of manganese. The resacetophenone oxime is not only stable in solution, but it also may be inserted into a hydrocolloid gel to facilitate a "spot test" for the detection of manganese, resulting in a long shelf life. These manganese testing methods disclosed herein may be used at the pre-disinfection process at water treatment facilities. The disclosed methods of manganese testing may be combined with an ammoniacal buffer reagent that may be used by water processing facilities, prior to final disinfection, to augment existing manganese (II) efforts of removal. A secondary flocculation with this buffer will scavenge additional manganese (II), that can then be removed by sedimentation or filtration.

As used herein, "multi-well plate" means a testing plate comprising two or more wells. Multi-well plates with 3, 9, 96 or other numbers of wells are possible. The applicants have developed a method of detecting manganese in a solution.

Using this method, the presence of manganese in the solution is detected using resacetophenone oxime as the detection agent. The presence of manganese in the solution will produce a yellow-brown color in when exposed to the resacetophenone oxime. To synthesize resacetophenone oxime, however, a precursor molecule, resacetophenone (RP), must first be synthesized. Although resacetophenone has been synthesized since the 19$^{th}$ century, its synthesis has been plagued by the production of impurities that reduce the yield of resacetophenone. For example, the synthesis of resacetophenone using acetic acid and a zinc chloride catalyst produces a red, resinous substance (the "red impurity"). Alternatively, the synthesis of resacetophenone using a zinc chloride catalyst with acids other than acetic acid, when combined with reduced pressure via vacuum distillation, produces resacetophenone with tan-colored crystal impurities (the "tan impurity"). While long-thought to be unwanted impurities, however, the applicants discovered that the red impurity and the tan impurity are, in fact, isomers of resacetophenone and can be used to synthesize resacetophenone oxime enantiomers, thereby increasing the yield of resacetophenone oxime production.

Figure 1:
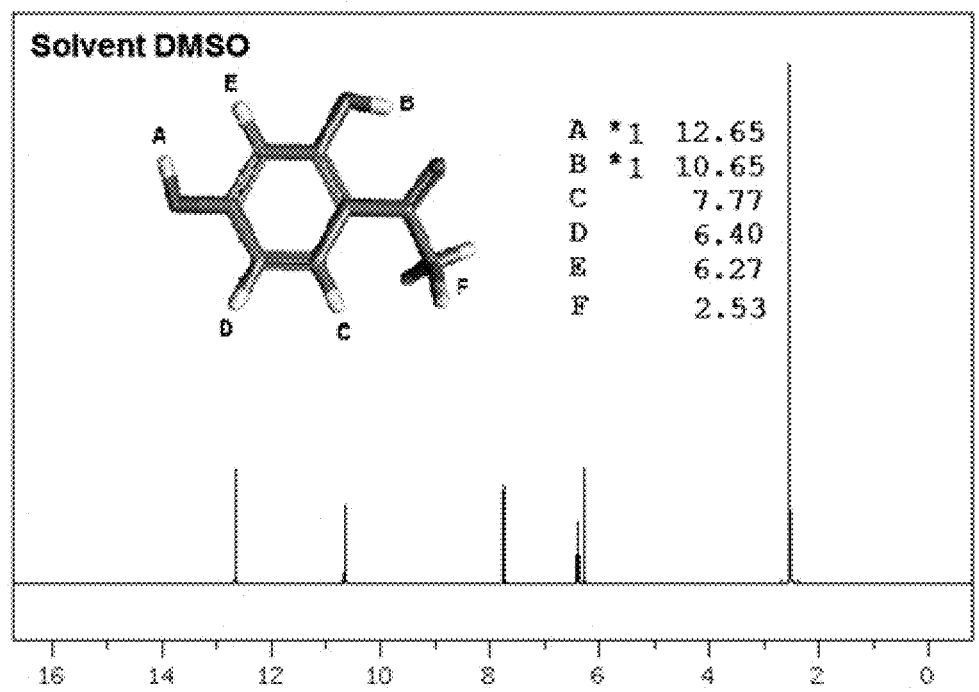
FIG. 1 displays proton NMR. (A) Proton NMR for commercial resacetophenone. (B) Proton NMR for the purified resacetophenone.
Figure 1:
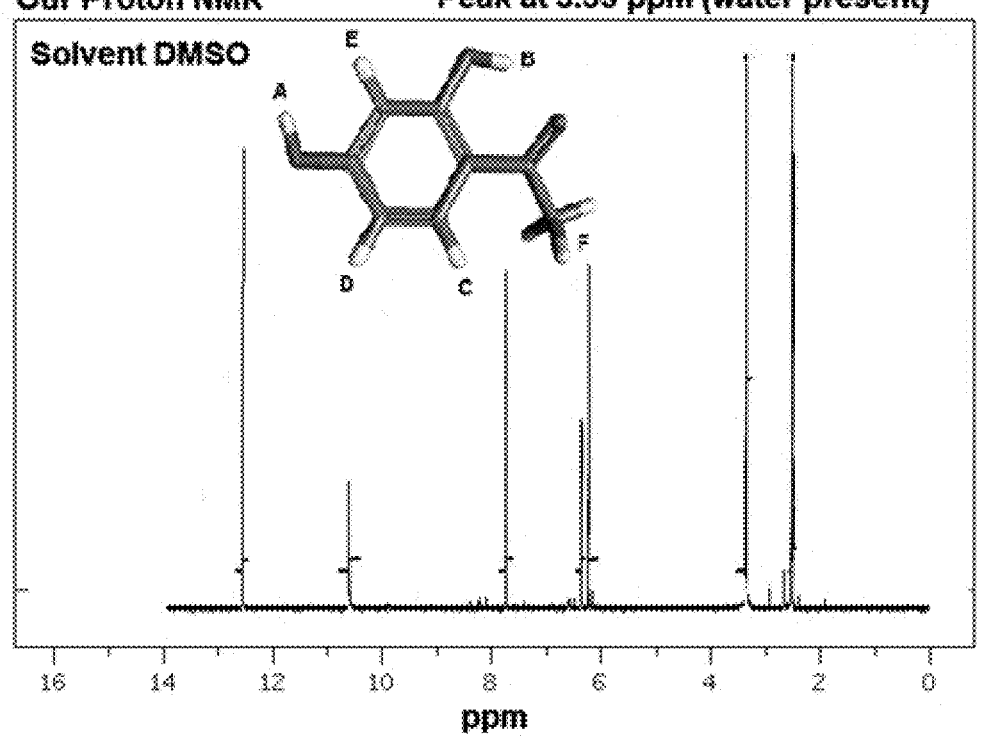

The applicants purified the red impurity and identified it as an isomer of resacetophenone by proton nuclear magnetic resonance (NMR) as shown in FIG. 1A (control: commercially-available resacetophenone) and FIG. 1B (test: red impurity). The applicants discovered that the red impurity was the same as commercially-available resacetophenone with only differences in conformation. Synthesis of resacetophenone oxime from the commercially-available resacetophenone results in a product that appears as a creamy yellow crystal. Synthesis of resacetophenone oxime from the red impurity results in a red crystal product, with production correlating both with temperature and duration. The creamy yellow crystal and red crystal products are enantiomers of resacetophenone oxime.

Figure 2:
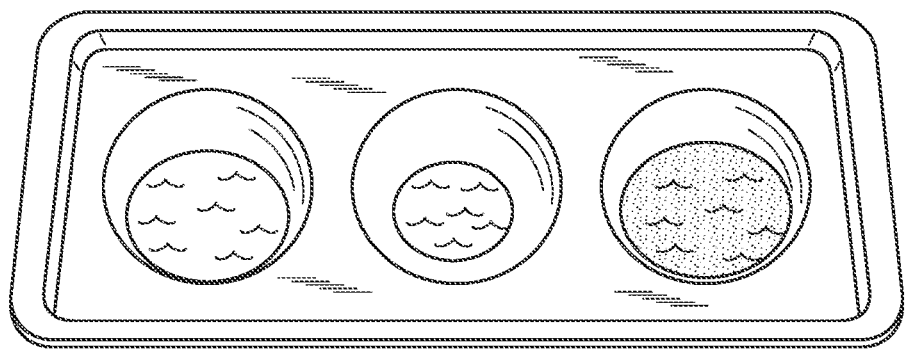
FIG. 2 depicts a three-well spot plate with control shown in the left-most well, distilled water shown in the center well, and a positive test shown in the right-most well.
Figure 3:
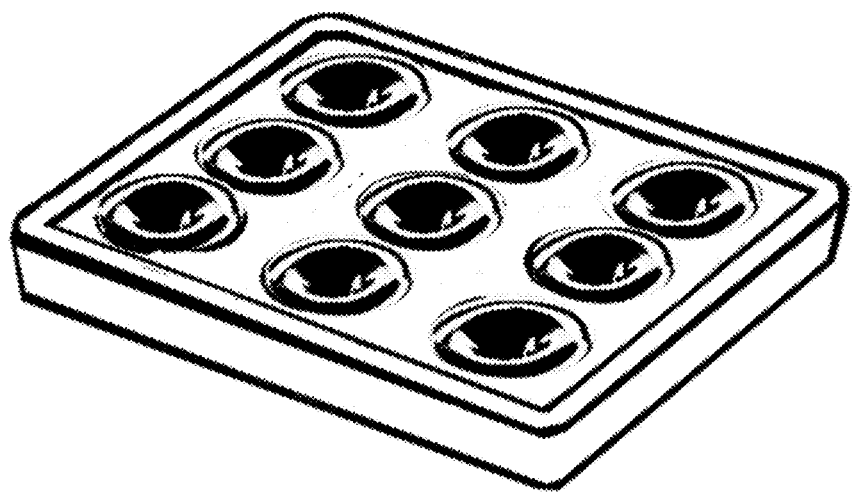
FIG. 3 depicts a nine-well spot plate for replicate testing.

Resacetophenone oxime enantiomers were synthesized from resacetophenone, purified and isolated, and using the purified resacetophenone oxime enantiomers (RPO), the applicants prepared low concentration stock solutions (0.2% w/v) by weight/volume of RPO in ammoniacal buffered 10% v/v ethanolic water. Alternatively, commercially-available resacetophenone oxime may be used. The RPO can be in solution in an equal volume of analyte water against control solutions (i.e., water samples without manganese (II)) to test for the detection of manganese (II) in solution. The detection of the presence of manganese using RPO is indicated by a yellow to brownish purple color change with the progression of color indicating a higher concentration of manganese. The testing method may be used in a multi-well plate assay, for example three-well spot plate assay as shown in FIG. 2, which comprises a negative control well (left-most well), a blank well containing distilled water (center well), and a positive-control RPO well (right-most well) wherein the positive-control RPO well indicated the presence of manganese in the solution as shown by a color change. The method may be performed by testing replicate samples to ensure accuracy. For example, FIG. 3 shows a nine-well spot plate that can be used for replicate testing.

To add stability to the manganese detection method and to alleviate the need to use liquid reagents, the method reagents may be stored within hydrocolloid gel thereby increasing shelf life storage of the reagents. The ideal hydrocolloid gel used in this process is gellan gum. Gellan gum is a water-soluble polysaccharide with a tetrasaccharide repeat unit of (D-Glucose)-(D-glucuronic acid)-(D-Glucose)-(L-Rhamnose)- and is abbreviated as [D-Glc(β1→4)D-GlcсA(β1→4) D-Glc(β1→4)L-Rha(α1→3)]n. The RPO and buffer may be stored in water-soluble gellan gum and provided as a small gel bead that can be placed in a depression spot well containing a control solution aliquot (without manganese (II)) and the analyte solution (possibly containing manganese (II)). The addition of water to the bead will cause dissolution of the gel and enable the RPO to react with the control and sample analytes. Gellan gum does not interact with the RPO and also does not interfere with spectrophotometric absorbance values in the wavelengths of interest for these assays. Furthermore, dissolution of the gel is not a requirement for a positive test, because the gel does not need to fully dissolve to give a positive test indication.

Spectrophotometric testing methods were developed to quantify manganese (II) in solution. In one embodiment of the method, resacetophenone oxime was prepared at a concentration of 0.2% w/v in 10% v/v ethanol water containing an ammoniacal buffer. The buffer pH may be between about 8.24 and 10.0. The buffer serves in two capacities. First, the buffer prevents the precipitation of manganese (II) as a hydroxide by keeping low concentrations soluble. Second, it is used to control the rate of reaction that enables attainment of the low threshold testing. A standard dilution series is utilized with each quantification protocol. The manganese (II) standard dilutions are made as dilutions from an approved Standards Company stock solution at a manganese (II) concentration of 1 g/L. A control sample containing zero micrograms of manganese (II) and five samples containing manganese (II) in a range between about 10 and 500 micrograms can be made as a dilution from the stock standard that include both 10 and 50 micrograms (the low threshold values for pharmaceutical water and bottled drinking water) as well as three other samples (e.g., 100, 250 and 500 micrograms of manganese (II) ion in solution). Other concentrations of manganese (II) standards may also be used. The sample to be tested may then be added to the resacetophenone oxime solution, incubated, and analyzed for a color change relative to the control standards to indicate the concentration of manganese present in the sample, if any. The method may be performed at room temperature. The method may also be performed by heating the solutions, for example with a thermal heater block incubator, to increase the temperature of the control solutions and the sample solution being tested above room temperature to increase the speed of the reaction of resacetophenone oxime with manganese.

Further, a buffer additive containing ammoniacal buffer in low concentration at higher pH may be used in water treatment facilities to remediate manganese (II), as a secondary capture following fluidized bed filtration. Prior to final chlorination, ammoniacal buffer may be used at pH 9.25 and above to scavenge for additional manganese (II) that can subsequently be filtered or sedimented from the water. The addition of buffer is offset by the fact that ammonia is often used to boost the effectiveness of chlorination, reducing the amount of chlorine needed.

These testing reagents and methods are considered green chemistry processes, conferring a substantial cost reduction in comparison to existing methods requiring special and expensive waste disposal consideration. The testing methods utilizing the resacetophenone oximes achieve the detection of manganese (II) in the low threshold target range using conventional UV-visible spectrophotometric methods. This enables the ability of even the smallest water treatment facilities to conduct in-house testing, immediate remediation when needed, and negates the need for outsourcing to costly laboratories. Producers of pharmaceutical quality and bottled waters also benefit by the use of a simple spectrophotometric method that does not require the use of highly skilled at higher cost PhD-level scientists currently needed for running the sophisticated testing methods currently used in industry.

Although the present invention and its advantages have been described in detail, it should be understood that various changes, substitutions and alterations can be made herein without departing from the spirit and scope of the invention as defined in the appended claims. The methods, assays, and the various embodiments thereof described herein are exemplary. Various other embodiments of the methods and assays described herein are possible.

Now, therefore, the following is claimed:

1. A method for testing for the presence of manganese in a sample solution, comprising the steps of:
    preparing at least one positive control, wherein the positive control contains manganese;
    preparing a negative control containing no manganese;
    adding resacetophenone oxime to the at least one positive control, negative control and the sample solution, wherein the resacetophenone oxime is contained within a hydrocolloid gel, wherein the hydrocolloid gel is configured to at least partially dissolve upon adding the resacetophenone oxime to the at least one positive control, negative control and the sample solution;
    incubating the at least one positive control, negative control and the sample solution; and
    measuring the at least one positive control, negative control and the sample solution for a colorimetric reaction, wherein a colorimetric reaction indicates the presence of manganese.

2. The method of claim 1, wherein the step of preparing at least one positive control comprises preparing a series of two or more positive controls, ranging in manganese concentration from about 10 to 500 micrograms.

3. The method of claim 2, wherein the positive controls comprise manganese concentrations of about 10, 50, 100, 250 and 500 micrograms.

4. The method of claim 1, wherein the resacetophenone oxime is at a concentration of 0.2% w/v in 10% v/v ethanol water containing an ammoniacal buffer.

5. The method of claim 4, wherein the ammoniacal buffer is at a pH between about 8.24 and 10.0.

6. The method of claim 1, wherein the method is performed at room temperature.

7. The method of claim 1, wherein the incubation step is performed above room temperature.

8. The method of claim 1, wherein the resacetophenone oxime added to the at least one positive control, negative control and the sample solution is at a concentration of about 1 g/L.

9. The method of claim 1, wherein the hydrocolloid gel comprises gellan gum.

10. The method of claim 1, wherein the step of measuring the at least one positive control, negative control and the sample solution for a colorimetric reaction is performed using spectrophotometry.

11. The method of claim 1, wherein the sample solution is obtained from a water supply.

12. The method of claim 11, wherein if a colorimetric reaction is observed in the sample solution, performing additional steps of adding ammoniacal buffer to the water supply, wherein the ammoniacal buffer is at a pH of at least 9.25, to sediment manganese and filtering the sedimented manganese from the water supply.

13. A kit for testing for the presence of manganese in a solution, comprising:
a manganese positive control;
a negative control containing no manganese; and
resacetophenone oxime, wherein the resacetophenone oxime is contained within a hydrocolloid gel.

14. The kit of claim 13, further comprising a multi-well plate.

15. The kit of claim 13, wherein the hydrocolloid gel comprises gellan gum.

* * * * *